(12) United States Patent
Huitema et al.

(10) Patent No.: US 7,699,860 B2
(45) Date of Patent: Apr. 20, 2010

(54) SURGICAL CLIP

(75) Inventors: Thomas W. Huitema, Cincinnati, OH (US); David B. Smith, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/907,770

(22) Filed: Apr. 14, 2005

(65) Prior Publication Data
US 2006/0235468 A1    Oct. 19, 2006

(51) Int. Cl.
A61B 17/04    (2006.01)
(52) U.S. Cl. ..................................... 606/158
(58) Field of Classification Search .............. 606/151, 606/153, 157, 158, 213, 215, 216, 221, 120, 606/142, 143; 227/902; 24/703.1, 30.5 W, 24/115 A, 20 CW, 129 W
See application file for complete search history.

(56) References Cited

U.S. PATENT DOCUMENTS

| | | | |
|---|---|---|---|
| 3,675,688 A | 7/1972 | Bryan et al. | |
| 3,775,825 A | 12/1973 | Wood | |
| 4,087,889 A * | 5/1978 | Ohba et al. | .............. 24/129 W |
| 4,188,953 A | 2/1980 | Klieman et al. | |
| 4,449,530 A | 5/1984 | Bendel | |
| 4,590,937 A * | 5/1986 | Deniega | .................... 606/158 |
| 4,702,247 A | 10/1987 | Blake, III et al. | |
| 4,799,481 A | 1/1989 | Transue et al. | |
| 4,844,066 A | 7/1989 | Stein | |
| 4,976,722 A * | 12/1990 | Failla | .......................... 606/157 |
| 4,979,950 A * | 12/1990 | Transue et al. | .............. 606/158 |
| 5,201,746 A | 4/1993 | Shichman | |
| 5,269,792 A | 12/1993 | Kovac et al. | |
| 5,282,808 A | 2/1994 | Kovac et al. | |
| 5,300,081 A | 4/1994 | Young et al. | |
| 5,358,506 A | 10/1994 | Green et al. | |
| 5,382,255 A | 1/1995 | Castro et al. | |
| 5,431,669 A | 7/1995 | Thompson et al. | |
| 5,501,693 A | 3/1996 | Gravener | |
| 5,509,920 A * | 4/1996 | Phillips et al. | .............. 606/157 |
| 5,527,319 A | 6/1996 | Green et al. | |
| 5,591,178 A | 1/1997 | Green et al. | |
| 5,626,585 A | 5/1997 | Mittelstadt et al. | |
| 5,626,592 A | 5/1997 | Phillips et al. | |
| 5,643,291 A | 7/1997 | Pier et al. | |

(Continued)

FOREIGN PATENT DOCUMENTS

EP    0 287 275    10/1988

(Continued)

OTHER PUBLICATIONS

European Search Report.

*Primary Examiner*—Anhtuan T Nguyen
*Assistant Examiner*—Tuan V Nguyen (57) ABSTRACT

A clip is provided that can be used for ligating tissue, such as vessels, other tubular ducts, and the like. The clip has opposed first and second leg members having proximal and distal ends. The proximal end of each leg member is connected by an apex having a notch formed therein. Moreover, each leg member has an inner tissue-contacting surface and an outer compression-receiving surface, both of which include features to provide a more secure ligation of the vessel or duct. A method of ligating vessels is also provided.

22 Claims, 7 Drawing Sheets

U.S. PATENT DOCUMENTS

| | | | |
|---|---|---|---|
| 5,645,551 A | 7/1997 | Green et al. | |
| 5,653,759 A * | 8/1997 | Hogan et al. | 606/78 |
| 5,700,271 A | 12/1997 | Whitfield et al. | |
| 5,713,911 A * | 2/1998 | Racenet et al. | 606/157 |
| 5,772,673 A | 6/1998 | Cuny et al. | |
| 5,792,149 A | 8/1998 | Sherts et al. | |
| 5,792,150 A | 8/1998 | Pratt et al. | |
| 5,833,696 A | 11/1998 | Whitfield et al. | |
| 5,843,101 A | 12/1998 | Fry | |
| 5,868,759 A | 2/1999 | Peyser et al. | |
| 5,904,693 A | 5/1999 | Dicesare et al. | |
| 5,928,251 A | 7/1999 | Aranyi et al. | |
| 5,938,667 A | 8/1999 | Peyser et al. | |
| 5,972,003 A | 10/1999 | Rousseau et al. | |
| RE36,720 E | 5/2000 | Green et al. | |
| 6,059,799 A | 5/2000 | Aranyi et al. | |
| 6,210,419 B1 * | 4/2001 | Mayenberger et al. | 606/158 |
| 6,241,740 B1 | 6/2001 | Davis et al. | |
| 6,306,150 B1 | 10/2001 | Levinson | |
| 6,537,289 B1 | 3/2003 | Kayan et al. | |
| 6,610,073 B1 * | 8/2003 | Levinson | 606/151 |
| 6,638,297 B1 | 10/2003 | Huitema | |
| 2002/0177863 A1 | 11/2002 | Mandel et al. | |
| 2003/0225423 A1 | 12/2003 | Huitema | |

FOREIGN PATENT DOCUMENTS

| | | |
|---|---|---|
| EP | 0 399 741 | 11/1990 |
| EP | 1481640 A1 | 12/2004 |

\* cited by examiner

FIG. 5E

SURGICAL CLIP

FIELD OF THE INVENTION

The present invention relates to surgical instruments, and in particular to surgical clips and methods used for ligating vessels, other ducts, and the like.

BACKGROUND OF THE INVENTION

During many surgical procedures, the surgeon will have to close or ligate various blood vessels and other ducts before severing them in order to prevent excessive bleeding, and reduce the risk of other complications to the patient. One ligation technique is to tie a suture about the vessel to close the vessel. Alternatively, a surgeon can place a clip having a pair of legs connected at their proximal ends about the vessel, and urge or squeeze the legs together to close the vessel.

One drawback associated with some current clips used for ligating vessels is that the legs of the clip may tend to separate to some extent following release from a clip applier. This phenomenon is called duck-billing. Duck-billing can result in insufficient ligation of a vessel, thus leading to excessive blood loss and/or unnecessary damage to the vessel. Further, some known ligation clips are often difficult to preload into a clip applier because of resistance between the tissue disposed between the jaws and the gripping features on the clip legs.

Accordingly, there remains a need for an improved surgical instrument and method, and in particular for surgical clips used for ligating blood vessels, other ducts, and the like.

BRIEF SUMMARY OF THE INVENTION

The present invention provides various methods and devices for ligating tissue, such as vessels, other ducts, and the like. In one aspect, a surgical clip is provided that includes a pair of opposed first and second leg members with a knee portion formed therebetween. While the apex can have a variety of configurations, in one embodiment, the apex can have opposed ends joining the proximal ends of said first and second leg members. Moreover, the apex can include a notch formed on an inner surface thereof.

The clip can have a variety of features that help provide a more secure ligation of the vessel. In one exemplary embodiment, the first and second leg members can include an inner surface having at least one tissue-grasping element formed thereon. The tissue-grasping elements can have a variety of configurations, such as a longitudinal tongue formed on the first leg member, and a longitudinal groove formed on the second leg member. The tongue and groove can be complementary and disposed opposite to each other. Moreover, the tongue and groove can extend along the entire length of the inner surface of each leg member, or a portion thereof. The tissue-grasping elements of the first and second leg members can also include at least one channel oriented at an angle with respect to the longitudinal axis of the first and second leg members.

In another exemplary embodiment, the first and second leg members can include an outer surface having at least one raised portion formed thereon. The raised portion can be a pad disposed on an outer surface of each of the first and second leg members located proximal to a point approximately midway between the apex and the knee portion of each leg member. In one embodiment, the raised area can be approximately one-third of the way between the apex and the knee, and closer to the apex.

In another aspect, a device for ligating tissue is disclosed having first and second leg members, with a knee portion formed therebetween. An apex can join the proximal ends of the first and second leg members, such that the first leg member and the second leg member are opposed from one another. While the apex can have a variety of configurations, in one exemplary embodiment, the apex includes a notch formed in an inner surface thereof.

In another aspect, a surgical clip is disclosed being in the form of a substantially U-shaped member that includes an apex that joins first and second leg members. The apex can further include a notch formed therein. In one exemplary embodiment, the leg members can include at least one tissue-grasping element formed on an inner surface thereof, and a knee portion formed between the proximal and distal ends thereof. Moreover, each leg member can have a width of less than about 0.05 inch, and a yield strength greater than about 28 ksi. In another exemplary embodiment, the clip can include a raised area disposed on an outer surface of each of the first and second leg members proximal to a point between the apex and the knee portion of each leg member. The raised area can be approximately one-third of the way between the apex and the knee, and closer to the apex.

In another aspect, a device for ligating tissue is provided having first and second opposed leg members with proximal and distal ends, and a knee portion formed between the proximal ends of each of the leg members. An apex having opposed ends joins the proximal and distal ends of the opposed leg members. The leg members further include inner and outer surfaces, the outer surface having at least one raised area on a portion thereof. In one embodiment, the raised area is located approximately one-third of the way between the apex and the knee portion, closer to the apex. In other embodiments, the device can further include at least one tissue-grasping feature formed on the inner surface of the opposed leg members, as well as a notch formed on the inner surface of the apex.

In another aspect, a ligation clip is provided having pair of opposed legs joined together at a proximal end by an apex. The opposed legs each can have a distal end and a knee portion disposed distal of the apex, and a raised area formed on an outer surface of each leg between the apex and the knee. The raised area is effective to share with the knee portions a load applied by a closing force such that the knee portions are subjected to less plastic deformation and retain some elasticity, wherein upon release of the closing force the distal ends of the clip remain in contact with one another.

A method for ligating vessels is also provided where a closing force is applied to each leg member such that in a partially closed position the knee portions of each leg member are substantially parallel to one another when the distal ends of each leg member are in contact with one another. As the closing force is continued to be applied to the clip, the raised areas and the knee portions share a load applied by the closing force such that the knee portions are subjected to less plastic deformation and retain some elasticity, wherein upon release of the closing force the distal ends of the clip remain in contact with one another.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
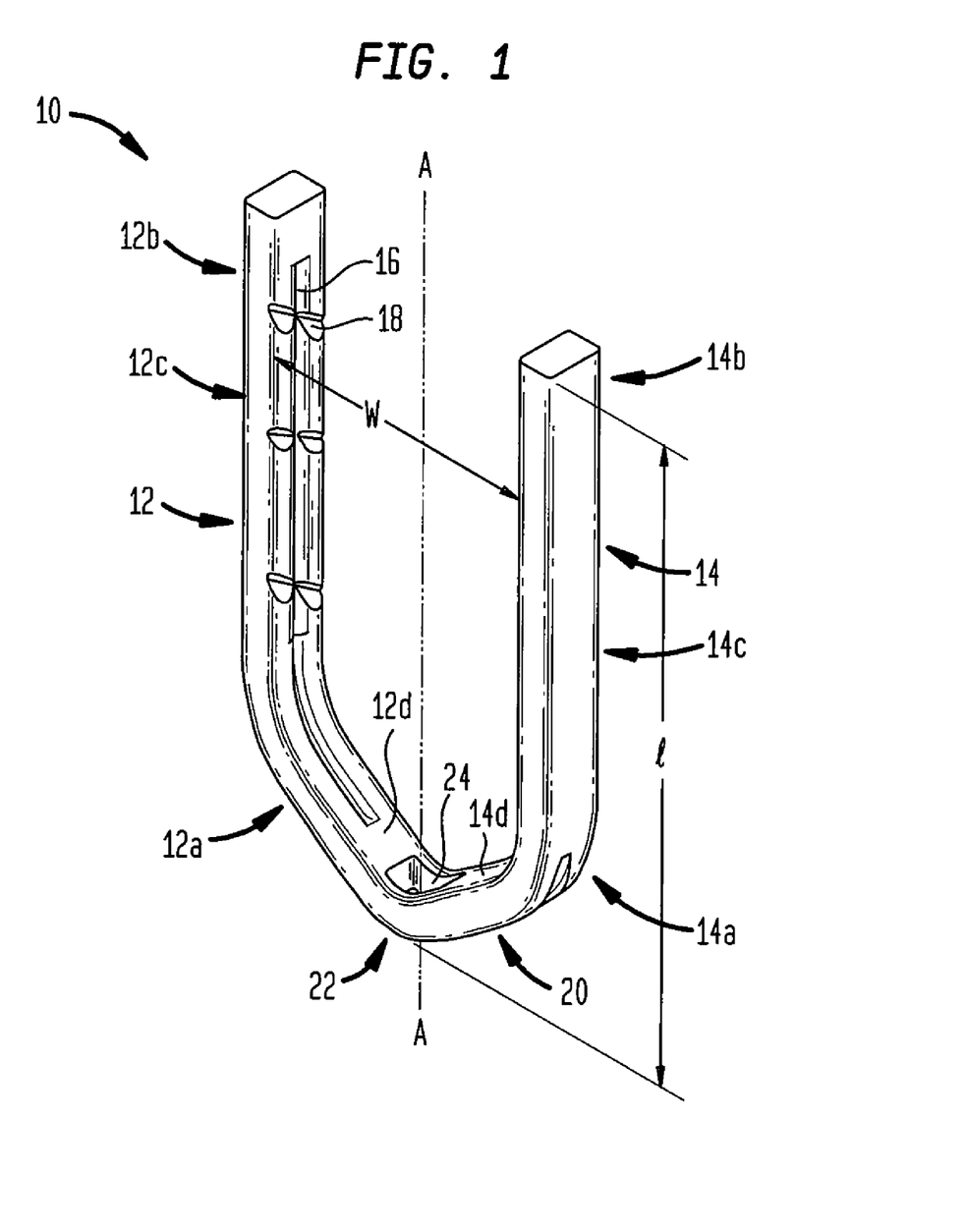
FIG. 1 is a perspective view of one embodiment of a surgical clip disclosed herein.

The present invention provides various devices for ligating tissue, such as vessels, other tubular ducts, and the like. FIGS. 1-4C illustrate exemplary embodiments of a clip disclosed herein in an open position. Referring generally to FIG. 1, the clip 10 in its open position is generally U-shaped having opposed leg members 12, 14 joined at an apex 22. Each leg member 12, 14 has a knee portion 20 disposed distally of the apex 22. Moreover, each leg member 12, 14 has an inner tissue-contacting surface 12d, 14d and an opposed outer surface 12c, 14c, both of which may have features to provide a more secure ligation of the vessel or duct. For example, the inner surface(s) 12d, 14d can include various tissue-grasping elements formed therein (discussed in more detail below). The outer surface(s) 12c, 14c can have at least one raised area 26 (shown in FIG. 3) formed thereon between the knee portion 20 and the apex 22. While the clip 10 of the invention is described herein in the context of a device to ligate vessels, one skilled in the art will appreciate that the surgical clip 10 of the present invention can be used to ligate a variety of other body tissues, including but not limited to, veins, arteries, ducts, or any other tubular member within a patient for which ligation is desired. Moreover, the clip 10 can be used in a variety of clip appliers, thereby effecting a wide range of surgical procedures. Although the clip 10 is described herein with respect to ligation, it is understood that a variety of other applications are possible as well.

The clip 10 can have any shape in its open configuration that allows it to effectively ligate a vessel, such as a substantially U-shaped or a substantially V-shaped design. As noted above, in an exemplary embodiment, the clip 10 is substantially U-shaped. That is, proximal portions 12a, 14a of the leg members 12, 14 of the clip 10 are oriented at an acute angle with respect to the central axis A of the clip 10, and transition at a knee portion 20, to an orientation where distal portions 12b, 14b of the leg members 12, 14 are parallel with respect to one another and to central axis A.

One skilled in the art will appreciate that the size of the clip 10 can vary depending upon its particular application. In an exemplary embodiment, the clip 10 can have a length/in the range of about 5 mm to 15 mm, and more preferably in the range of about 7.5 mm to 8.5 mm. In its open configuration, the clip 10 can have a width W as shown in FIG. 3 measured between opposed inner surfaces 12d, 14d of the leg members 12, 14 in the range of about 2 mm to 8 mm, and more preferably in the range of about 3 mm to 4 mm. The size of the leg members 12, 14 can also vary depending upon the particular application, however in one embodiment, each leg member 12, 14 can have a width w, shown in FIGS. 2D and 2E, less than 0.050 inch, more preferably in the range of about 0.025 inch to about 0.040 inch, most preferably less than about 0.035 inch. Moreover, each leg member 12, 14 can have a height H (shown in FIG. 3) in the range of about 0.015 inch to 0.030 inch, and more preferably in the range of about 0.018 inch to 0.025 inch, and most preferably in the range of about 0.019 inch to 0.020 inch.

The clip can also have physical properties, such as yield strength, that are appropriate for a desired application. In an exemplary embodiment, the yield strength is greater than about 28 ksi and less than about 60 ksi, and more preferably in the range of about 30 ksi to 50 ksi. In general, the clip 10 constructed according to the present invention has a yield strength that is equivalent to or greater than clips having larger dimensions.

The clip 10 of the present invention is further designed so that, upon closure, a vessel, for example, is completely encased between the leg members 12, 14 of the clip 10. This is done by urging the leg members 12, 14 of the clip 10 together, typically with the assistance of an applier, to surround the vessel.

Referring now to FIGS. 2A-2E, the clip 10 has opposed first and second leg members 12, 14 each having proximal and distal ends 12a, 14a, 12b, 14b. The proximal and distal ends 12a, 14a, 12b, 14b have opposed inner tissue-contacting surfaces 12d, 14d and outer compression-receiving surfaces 12c, 14c that are connected by superior and inferior sides 12e, 14e, 12f, 14f. One skilled in the art will appreciate that the leg members 12, 14 can have any cross-sectional shape that allows them to effectively close and engage tissue, such as a vessel. Exemplary cross-sectional shapes include, but are not limited to, triangular, rectangular, trapezoidal, and pentagonal. As shown, however, the leg members 12, 14 are substantially rectangular. The substantially rectangular leg shape is believed to provide an optimized design that includes a greater bending resistance for a given clip leg space envelope.

The leg members 12, 14 can also have a variety of features formed therein or thereon to assist with the ligation of a vessel or duct. For example, the inner surface 12d, 14d of each leg member 12, 14 can include tissue-grasping elements, and the outer surface 12c, 14c of each leg member 12, 14 can include a knee portion 20 as well as at least one raised area 26. Optionally, one or more grooves may be formed on the outer surface 12c, 14c as well.

As shown in FIGS. 2A-2E, the tissue-grasping elements formed on an inner surface 12d, 14d of each leg member 12, 14 can include both primary 16, 17 and secondary 18 tissue-grasping elements. The primary tissue-grasping elements 16, 17 can have any configuration that allows them to effectively hold a vessel or duct. In one embodiment, the primary tissue-grasping elements can include at least one tongue 17 formed on the inner surface 14d of the second leg member 14 and at least one groove 16 formed on the inner surface 12d the first leg member 12. The groove 16 and tongue 17 can extend continuously along the inner surface 12d, 14d of each leg member 12, 14. Alternatively, the inner surface 12d, 14d can include multiple groove 16 and tongue 17 segments formed therein.

The groove 16 and tongue 17 can be formed in a variety of locations on each of the first and second leg members 12, 14. In one embodiment, the groove 16 and tongue 17 can extend longitudinally along the entire length or along at least a portion of the length of the inner surface 12d, 14d of each respective leg member 12, 14. Alternatively, the groove 16 and tongue 17 can extend from the distal end 12b, 14b of each leg member 12, 14 to just distal from the apex 22, or from the distal end 12b, 14b of each leg member 12, 14 to just distal to the knee portion 20. Moreover, the groove 16 and tongue 17 can extend distally from the apex 22 to a position just distal to the knee portion 20.

Figure 2A:
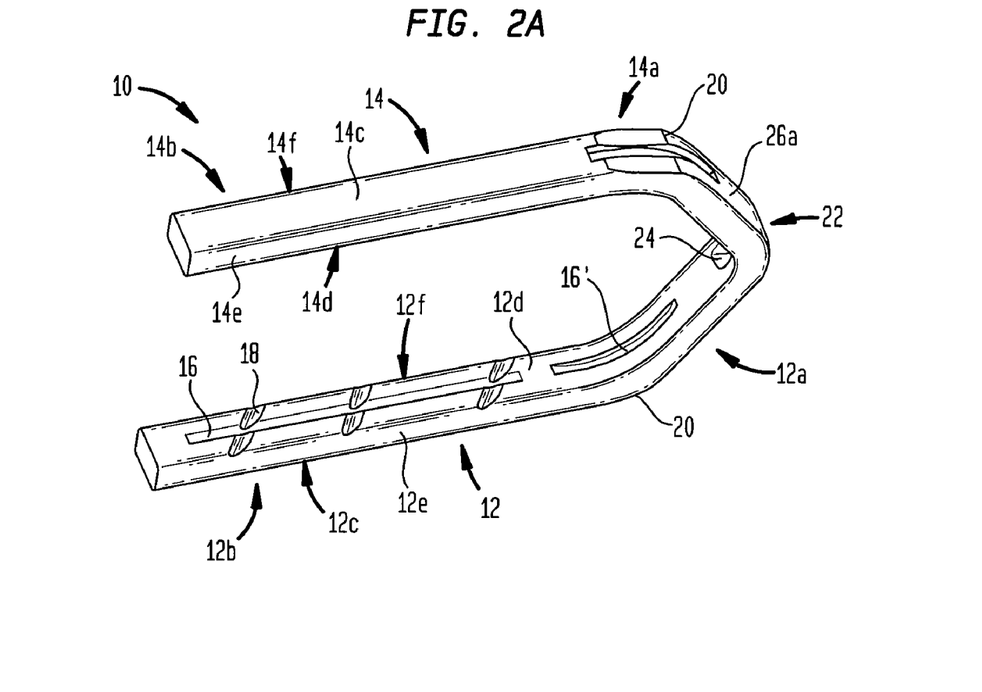
FIG. 2A is a side perspective view of a clip according to another embodiment of the invention.
Figure 4A:
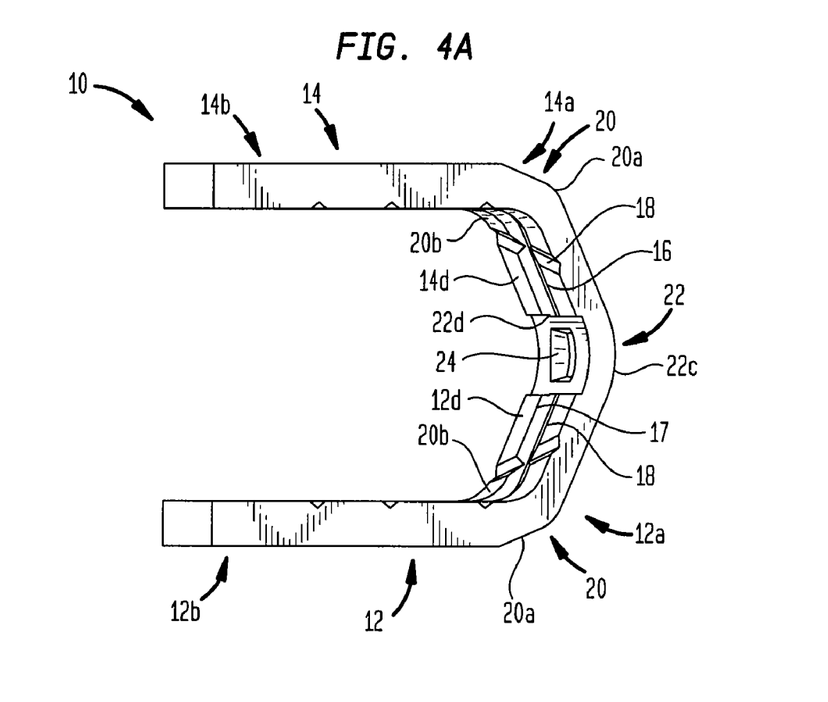
FIG. 4A is a perspective view of a clip according to the invention.

By way of non-limiting example, FIG. 1 illustrates a longitudinal groove 16 and a longitudinal tongue 17 that extend through the knee portion 20 and terminate just distal to the notch 24 in the apex 22. Alternatively, FIG. 2A illustrates a longitudinal groove 16 and a longitudinal tongue 17 that extend from the distal end 12b, 14b of each leg member 12, 14 to a position just distal to the knee portion 20. A second longitudinal groove 16' and longitudinal tongue 17' combination is then formed just distal to the knee portion 20, extending just distal to the apex 22. Moreover, FIG. 4A illustrates a longitudinal groove 16 and a longitudinal tongue 17 that are formed along the entire inner surface 12d, 14d of each of the first and second leg members 12, 14. The groove 16 and tongue 17 combination shown in FIG. 4A terminates in the notch 24 of the apex 22, as will be discussed in more detail below.

The tongue 17 and groove 16 can be disposed so as to be complementary to one another. Alternatively, the tongue 17 and groove 16 can be located at different locations along each respective leg member 12, 14. In an exemplary embodiment, the tongue 17 are groove 16 are complementary and disposed opposite one another, such that once the clip 10 is applied to a vessel the tongue 17 will urge the tissue of the walls of blood vessel into the corresponding juxtaposed groove 16. This cooperation between the tongue 17 and the groove 16 inhibits longitudinal and angled dislocation of the clip 10 relative to the vessel, and it also effectively reduces the gap between the inner (tissue contacting) surfaces of each respective leg member 12, 14.

Figure 2B:
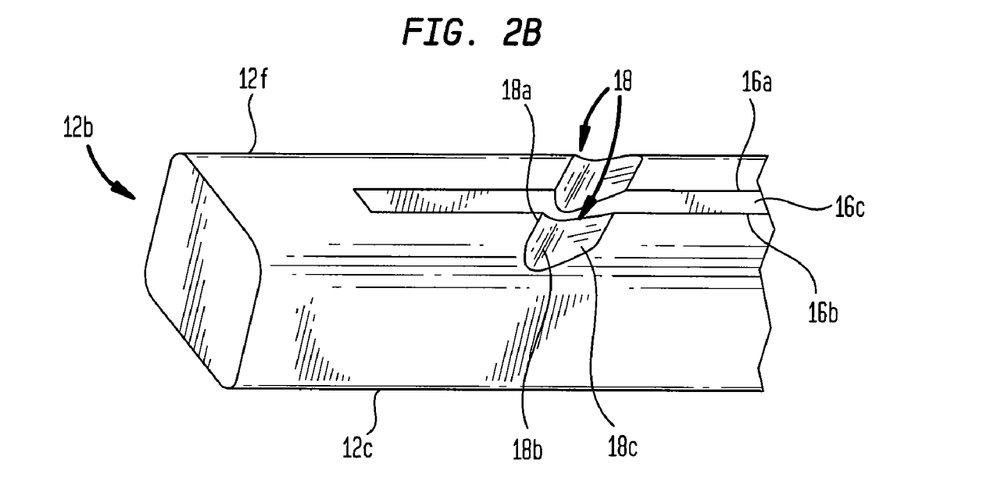
FIG. 2B is a side perspective view of a portion of the distal end of a leg member of the clip of FIG. 2A.
Figure 2C:
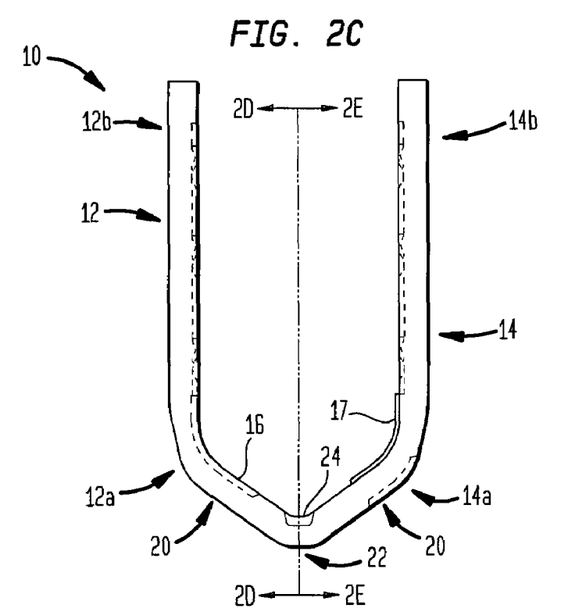
FIG. 2C is a plan view of the clip of FIG. 2A.

One skilled in the art will appreciate that the groove 16 can have a variety of shapes. In an exemplary embodiment, the groove 16 is complementary in shape to the tongue 17 and can be hemispherical, rectangular, triangular, trapezoidal, or oblong. As shown in FIG. 2B, an exemplary embodiment uses a groove 16 that is somewhat triangular, having opposed sidewalls 16a, 16b connected by a base portion 16c. The sidewalls 16a, 16b can be oriented at various angles with respect to the inner surface 12d, 14d of the leg members 12, 14. In one embodiment, the sidewalls 16a, 16b are oriented at an angle less than 120 degrees relative to the inner surface 12d, 14d of the leg members 12, 14, and more preferably at an angle less than 110 degrees relative to the inner surface 12d, 14d of the leg members 12, 14.

One skilled in the art will appreciate that the base portion 16c can have a variety of configurations. For example, the base portion 16c can be planar or slightly rounded. In an exemplary embodiment, however, the base portion 16c is slightly rounded.

One skilled in the art will appreciate that the groove 16 should be of dimensions that are effective to ligate tissue. For example, the groove 16 can have depths in the range of about 0.0015 inch to 0.007 inch, more preferably, in the range of about 0.0025 inch to 0.004 inch. In one exemplary embodiment, the groove 16 can have a depth of about 0.0025 inch. Further, groove 16 can have a width in the range of about 0.004 inch to 0.020 inch, more preferably in the range of about 0.006 inch to 0.013 inch. Moreover, the width of the groove 16 can be uniform throughout the length of the groove 16, or it can decrease in the proximal or distal direction. In an exemplary embodiment, the groove 16 has a uniform width.

One skilled in the art will also appreciate that the tongue 17 can also have a variety of configurations. However, in an exemplary embodiment, the tongue 17 is complementary in shape and size to the groove 16. Thus, the tongue 17 can be hemispherical, rectangular, triangular, trapezoidal, or oblong. In an exemplary embodiment, the tongue 17 is substantially rectangular or trapezoidal.

The tongue 17 can also vary in size, however in an exemplary embodiment, the tongue 17 has a size that is complementary to the size of the groove 16, with a height and a width no greater than, and preferably slightly less than, the dimensions of the groove 16. This provides room for the vessel tissue and minimizes shearing action and locally excessive pressures on the vessel tissue during clip forming. That is, the tongue 17 can have a height in the range of about 0.0015 inch to 0.007 inch, more preferably in the range of about 0.0025 inch to 0.004 inch. In one exemplary embodiment, the tongue 17 can have a height of about 0.0025 inch. The tongue 17 can also have a width in the range of about 0.004 inch to 0.020 inch, more preferably in the range from about 0.006 inch to 0.013 inch. Moreover, and also similar to the groove 16 above, the tongue 17 can have a uniform width or a width that decreases in the proximal or distal direction. In an exemplary embodiment, the tongue 17 has a uniform width.

In addition to primary tissue-grasping elements 16, 17, the inner surfaces 12d, 14d of each of the first and second leg members 12, 14 can have at least one secondary tissue-grasping element 18, as shown in FIG. 2B. While in one embodiment the secondary tissue-grasping elements 18 are formed on the inner surfaces 12d, 14d of both the first and second leg members 12, 14, the secondary tissue-grasping element 18 can optionally be formed on the inner surface 12d, 14d of only one of the first and second leg members 12, 14. One skilled in the art will appreciate that the inner surfaces 12d, 14d of the first and second leg members 12, 14 can have any number of secondary tissue-grasping elements 18. In the exemplary embodiment, the inner surface 12d, 14d has at least four secondary tissue-grasping elements 18.

The secondary tissue-grasping elements 18 can have any configuration that allows them to grasp tissue following application of the clip to the vessel or duct. As shown in FIG. 2B, exemplary secondary tissue-grasping elements 18 are in the form of channels having opposed first and second walls 18a, 18b connected by base wall 18c. The channels are generally saw-toothed in shape, however can also be undercut. In an exemplary embodiment, the first wall 18a is formed at an acute angle relative to the inner surface 12d, 14d of each leg member. In an exemplary embodiment the angle is in the range of about 40 degrees to 90 degrees, and more preferably the angle is about 75 degrees. The second wall 18b is likewise oriented at an acute angle relative to the inner surface 12d, 14d of each leg member. The acute angle of the second wall 18b, which is generally shallower than the angle of the first wall 18a, can be in the range of about 15 degrees to about 75 degrees, and more preferably it is about 45 degrees. One skilled in the art will appreciate that the walls 18a, 18b, 18c can be straight or arcuate, but in the exemplary embodiment the walls 18a, 18b, 18c are slightly arcuate to facilitate grasping.

Figure 2D:
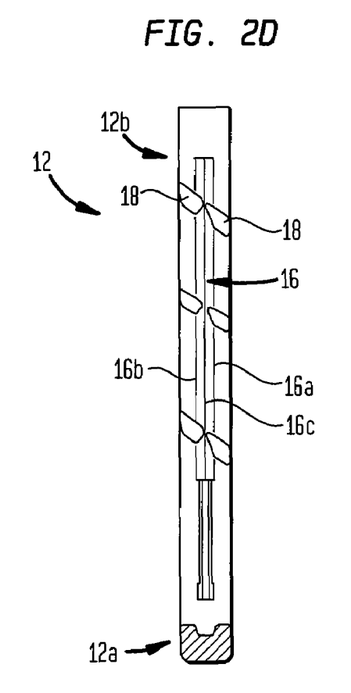
FIG. 2D is a sectional view of the clip of FIG. 2C along the lines 2D-2D.
Figure 2E:
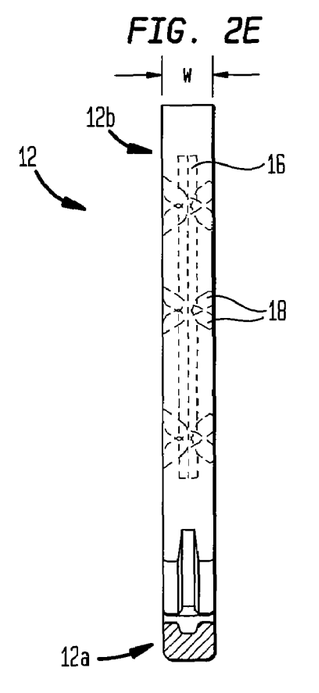
FIG. 2E is a sectional view of the clip of FIG. 2C along lines 2E-2E.
Figure 3:
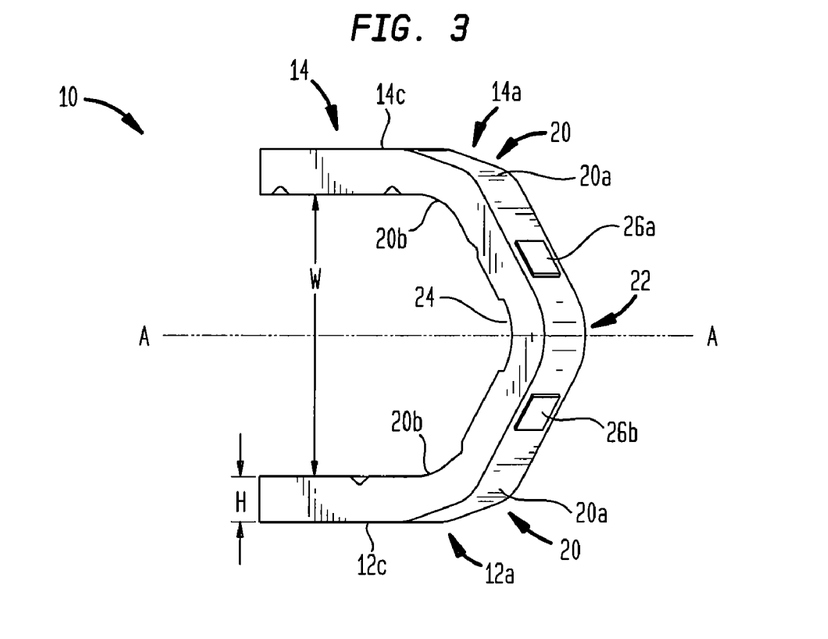
FIG. 3 is another perspective view of a clip according to the invention.

As shown in FIGS. 2D-2E, the secondary tissue-grasping elements 18 extend across the width w of the first and second leg members 12, 14 at an angle (e.g., about 45 degrees) relative to a longitudinal axis of the leg members 12, 14. In an exemplary embodiment, one segment of the secondary tissue-grasping element 18 is located on one side of the tongue 16 or groove 17 on the first leg member 12, and a second segment 18 continues at the same angle on the other side of the tongue 16 or groove 17. The secondary tissue-grasping elements 18 are similarly constructed on the second leg member 14, however they are angled at an orientation opposite that of the first leg member 12. Thus, when the leg members 12, 14 close around a vessel or duct, they form a superimposed "x," as shown in FIG. 2E. This configuration allows for a greater percentage of the tissue to be grasped by the secondary tissue-grasping elements 18, thereby resulting in more effective ligation.

The leg members 12, 14 can have any number of secondary tissue-grasping elements 18 formed thereon. In the exemplary embodiment, however each leg member 12, 14 has three secondary tissue-grasping elements 18 formed thereon. One skilled in the art will appreciate that the secondary tissue-grasping elements 18 can be uniformly or non-uniformly spaced apart from one another. In an exemplary embodiment, the secondary tissue-grasping elements 18 are uniformly spaced apart from one another at a distance in the range of about 0.050 inch to 0.080 inch. Moreover, the secondary tissue-grasping elements 18 can have any size and depth that is effective to engage and maintain contact with tissue. However, in an exemplary embodiment, the secondary tissue-grasping elements 18 are sized in the range of about 0.008 inches to 0.012 inches wide by about 0.0015 inches to 0.0035 inches deep.

One skilled in the art will appreciate that the leg members 12, 14 of the exemplary clip 10, as shown in FIGS. 1-4C, can include any combination of primary tissue-grasping elements 16, 17 and secondary tissue-grasping elements 18. An exemplary clip 10, however, includes both primary and secondary tissue-grasping elements 16, 17, 18. In another exemplary embodiment (not shown), the inner surface 12d, 14d of the leg members 12, 14 can be smooth and free of primary and secondary tissue-grasping elements. The structure and closing properties of the clip 10, as discussed herein, allow adequate tissue ligation without the need for any type of tissue-grasping elements formed on the inner surface 12d, 14d of the leg members 12, 14.

As shown, for example, in FIG. 3, the outer surface 12c, 14c of each leg member 12, 14 can include a bend or knee portion 20. The knee portion 20 allows the leg members 12, 14 to transition from being acutely angled relative to the central axis A of the clip 10 to being substantially parallel relative to one another and to the central axis A of the clip 10. The angled knee portions 20 of the leg members 12, 14 can be formed at a variety of angles relative to the central axis A of the clip 10, however in an exemplary embodiment the angle can be in the range of about 45 degrees to about 65 degrees. In one embodiment, the knee portion 20 is designed so as to be parallel to the force applying jaws of a clip applier during a part of the clip closing process as shown in FIG. 5B. This construction is believed to enhance clip retention by the clip applier during deployment.

The knee portion 20 can have a variety of configurations to effect the transition of the leg members 12, 14, however an exemplary knee portion 20 has a beveled or flattened outer surface 20a and an arcuate inner surface 20b. The bevel on the outer surface 20a can extend over any length sufficient to effect the transition, however in an exemplary embodiment the bevel is in the range of about 0.030 inch to 0.050 inch. The outer surface 20a of the knee portion 20 can optionally include a groove (not shown) formed therein to facilitate formation of a raised tongue 17 on the inner surface 12d, 14d of the leg members 12, 14. The groove can be similar in shape and size to the longitudinal groove 16, discussed herein with respect to FIGS. 2A-2E. The inner surface 20b of the knee portion 20 can also optionally include features to assist with the ligation of the vessel, duct, or tissue. For example, the inner surface 20b can include primary and/or secondary tissue-grasping elements 16, 17, 18 similar to those discussed above with respect to FIGS. 2B-2D.

As noted above, the outer surface 12c, 14c of each leg member 12, 14 can have features to help provide a more secure occlusion and clip performance. In one embodiment, shown in FIG. 3, a raised area 26 extends over a portion of the width of the leg members 12, 14 that is slightly proximal to the knee portion 20. In an exemplary embodiment, the raised area 26 is located approximately one-third of the way between the apex 22 and the knee portion 20, closer to the apex 22. The raised portion 26 is believed to help to reduce overbending of the knee 20 as well as to help maintain the legs 12, 14 of the clip 10 together after the clip 10 is fully closed. While FIG. 3 shows the raised area 26 formed on both the first and second leg members 12, 14, in alternate embodiments, the raised area 26 can be formed on either the first leg member 12 or the second leg member 14. Moreover, the outer surface 12c, 14c of each leg member 12, 14 can have any number of raised areas 26. In the exemplary embodiment, the outer surface 12c, 14c of each leg member 12, 14 has one raised area 26a, 26b.

The raised area 26a, 26b can have any shape that allows the effective application of compressive force to the apex 22 such that the apex 22 is crimped to a greater degree than the knee portion 20. That is, the raised area 26a, 26b is believed to allow the region of the leg member 12, 14 between the apex 22 and the knee 20 to be more elastic, enabling the knee portion 20 to spring back to a small degree while maintaining adequate contact between the distal ends 12b, 14b of the leg members 12, 14. In an exemplary embodiment, the raised area 26a, 26b is a pad having a shape that is complementary to the shape of the leg member 12, 14. Thus, the raised area 26a, 26b can be triangular, rectangular, trapezoidal, pentagonal, etc., but in an exemplary embodiment, the raised area 26a, 26b is substantially rectangular.

One skilled in the art will appreciate that the raised area 26a, 26b can have a variety of sizes, depending upon whether full closure or partial closure of the clip is desired. By way of non-limiting example, if full closure of the clip is desired, the height of the raised area 26a, 26b should be able to maintain the preload at the distal tips of the leg members 12, 14. In an exemplary embodiment, the raised area 26a, 26b has a height in the range of about 0.0005 inch to 0.0025 inch, and more preferably is about 0.001 inch. The raised area 26a, 26b can also have a length that is large enough so that it can adequately sustain the applied pressure from a clip applier. In an exemplary embodiment, the raised area 26a, 26b can have a length of about 0.020 inch, and a width of about 0.010 inch. If partial closure of the clip is desired, the height of the raised area 26a, 26b can be increased.

Figure 4B:
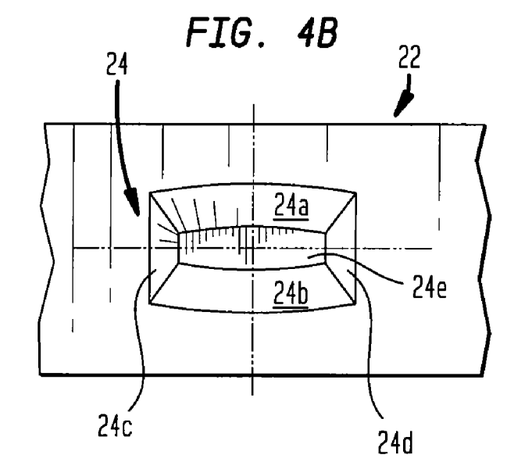
FIG. 4B is a top plan view of an inner portion of the apex of the clip of FIG. 4A.
Figure 4C:
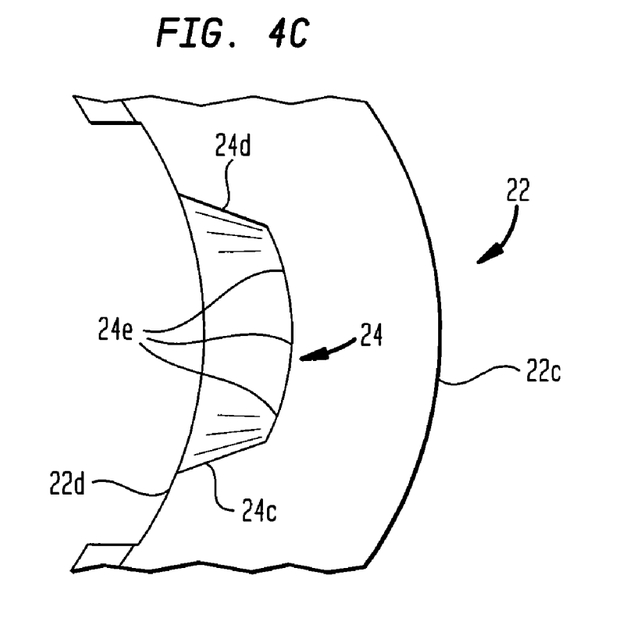
FIG. 4C is a side perspective view of an inner portion of the apex of the clip of FIG. 4A.

As noted above, the proximal ends of each of the leg members 12a, 14a are connected to one another by an apex 22. While the apex 22 can have a variety of shapes, as shown in FIGS. 4A-4C, the apex 22 is substantially U-shaped or substantially V-shaped, and has opposed inner (tissue-contacting) 22d and outer (non-tissue contacting) faces 22c that are connected by superior and inferior surfaces (not shown).

The inner surface 22d of the apex 22 can have a variety of configurations in order to assist with ligation, for example, at least one notch 24 can be formed therein. While the inner surface 22d can have any number of notches formed therein, an exemplary embodiment utilizes one notch 24. One skilled in the art will appreciate that the notch 24 can have any configuration that allows for the ligation of tissue. In an exemplary embodiment, the notch 24 is formed in a U-shaped channel that extends through the inner surface 22d of the apex 22. The U-shaped channel may join the tongue 16 and groove 17 that extend along at least a portion of length of the inner surface 12d, 14d of the leg members 12, 14.

The notch 24 can further have a variety of shapes to optimize its mechanical properties and make it stiff and strong for the amount of material in it, yet leaving open space for the material in compression on the inner side of the clip 10 to flow into during the plastic deformation that occurs during clip formation. In an exemplary embodiment, as shown herein, the notch 24 is substantially trapezoidal. That is, as shown in FIGS. 4B-4C, the notch 24 has opposed first and second walls 24a, 24b connected by opposed third and fourth walls 24c, 24d with a base portion 24e extending therebetween. While the walls 24a, 24b, 24c, 24d can have a variety of configurations, in an exemplary embodiment the walls 24a, 24b, 24c, 24d are formed at an acute angle relative to the inner surface 22d of the apex 22. The angle can be any acute angle, but it is preferably in the range of about 75 degrees. One skilled in the art will appreciate that the walls 24a, 24b, 24c, 24d, 24e can have also have any shape that provides an area into which deformed tissue can flow. As shown, the walls and the base portion 24a, 24b, 24c, 24d, 24e are rounded or slightly contoured.

The notch 24 can have a variety of sizes and depths, perhaps best described in relationship to the thickness and width of the clip leg members 12, 14. The width of notch 24 should be such that the webs of material at apex surface 22d are in the range of about 0.005 inch to 0.010 inch wide. The depth of notch 24 should be in the range of about 30 percent to 60 percent of the distance between apex surfaces 22c and 22d, with an exemplary range of about 30 percent to 40 percent of the distance between surfaces 22c and 22d. The length of notch 24 should be in the range of about 1 times to 2 times the thickness of the clip leg members 12, 14, with an exemplary length in the range of about 1.1 times to 1.4 times the thickness of the clip leg members 12, 14. In the case of larger, wider clips, optimum results might require the use of two or more notches in order to maintain the webs of material at surface 22d in the range of about 0.005 inch to 0.010 inch. Other aspects of multiple notches would be expected to follow the guidelines listed above.

The outer face 22c of the apex 22 can also have a variety of configurations in order to assist with ligation. In an exemplary embodiment, the outer face of the apex 22c has two opposed beveled surfaces that meet in a rounded tip. The outer face 22c of the apex 22 is not sharply formed, but rather has a fabrication-induced radius, thereby allowing for a more secure ligation.

The clip 10 disclosed herein can be made from a variety of surgically-appropriate materials including metals and polymers. Moreover, the material can be a bioabsorbable material or a non-bioabsorbable material. In one embodiment, the clip 10 can be made of a metal or a metal alloy having a relatively high annealed state yield strength and a relatively high strain hardening rate, in comparison to existing ligation clips. Suitable metals include tantalum, titanium, stainless steel, or alloys thereof. By way of non-limiting example, the clip 10 can be made from commercially pure titanium or ASTM grade CP1 titanium. This material, when compared with conventional materials, is able to be strain hardened to a greater extent without causing excessive gaps in the formed clip 10.

Moreover, a small amount of interstitial elements, such as oxygen or nitrogen, can be added to the clip material to maintain the formability of the clip 10. In an exemplary embodiment, oxygen can be incorporated within the clip material. Other interstitial elements can include nitrogen, carbon, and iron. The clip 10 can also optionally be coated with an antimicrobial or antibiotic material in order to increase the effectiveness of the clip against a broad range of infectious agents or pathogens.

Figure 5A:
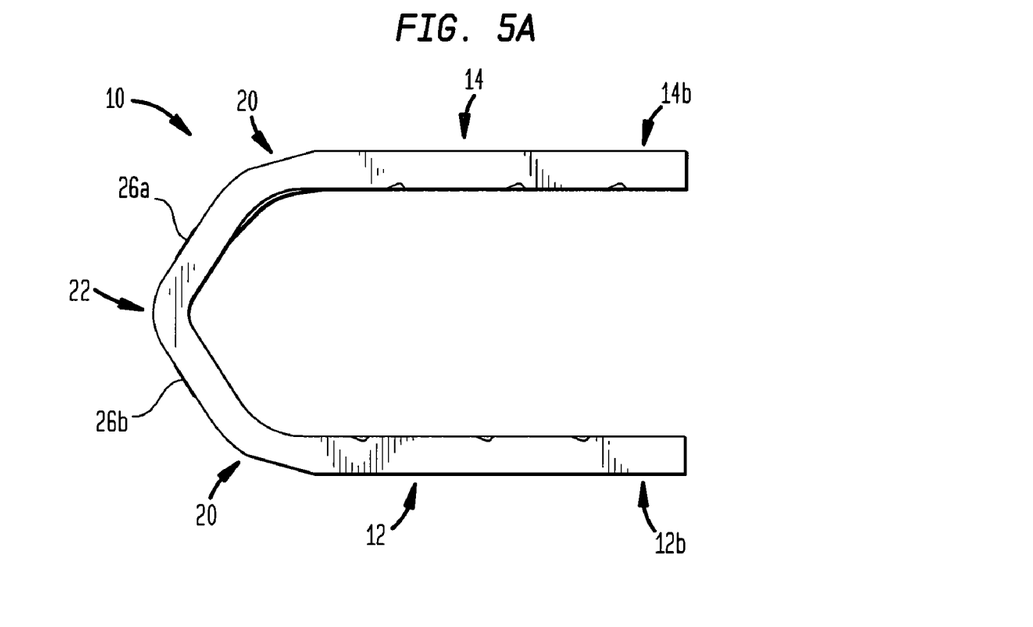
FIG. 5A is another side perspective view of a clip according to the invention in an open position.
Figure 5B:
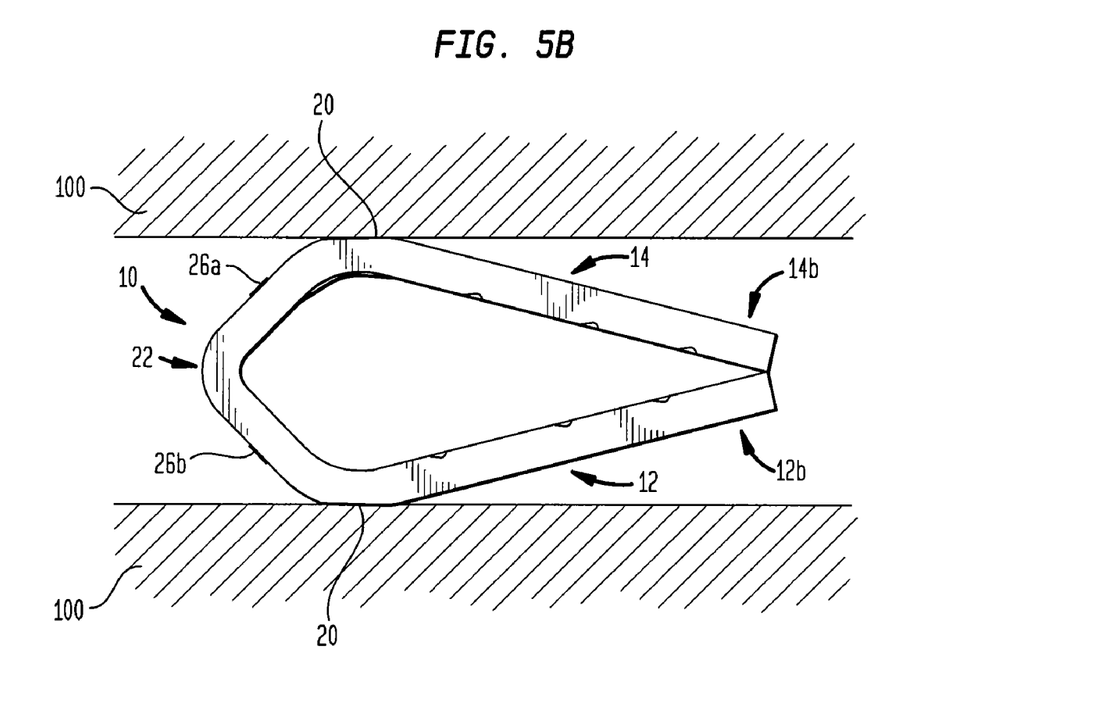
FIG. 5B is a side perspective view of the clip of FIG. 5A in a first state of partial closure.

FIGS. 5A-5E sequentially illustrate selected steps of clip closure, for example to ligate a vessel. As shown in FIG. 5A, an open clip 10 is presented, and it can be placed around a desired vessel. A closing force is then applied to the outer surface 12c, 14c of the leg members 12, 14 by, for example, the force-applying jaws 100 of a clip applier. As clip closure begins, as shown in FIG. 5B, the knee portion 20 and the apex 22 are deformed such that the distal ends 12b, 14b of the leg members 12, 14 are moved inward towards one another. In the position shown in FIG. 5B, the clip features at the knees 20 have become predominately parallel to each other and to the clip applying jaws 100, helping to stabilize the clip 10 in the jaws 100 of the applier.

Figure 5C:
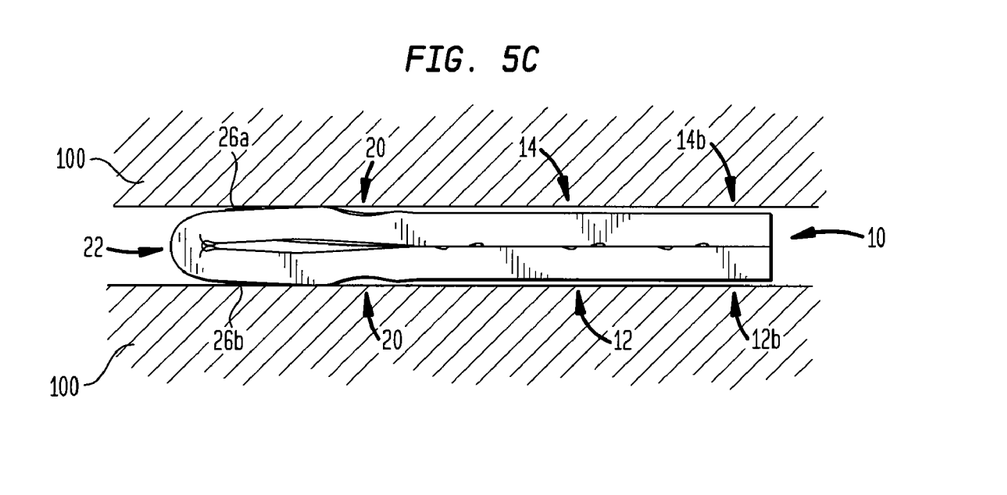
FIG. 5C is a side perspective view of the clip of FIG. 5A in a state of almost full closure.
Figure 5D:
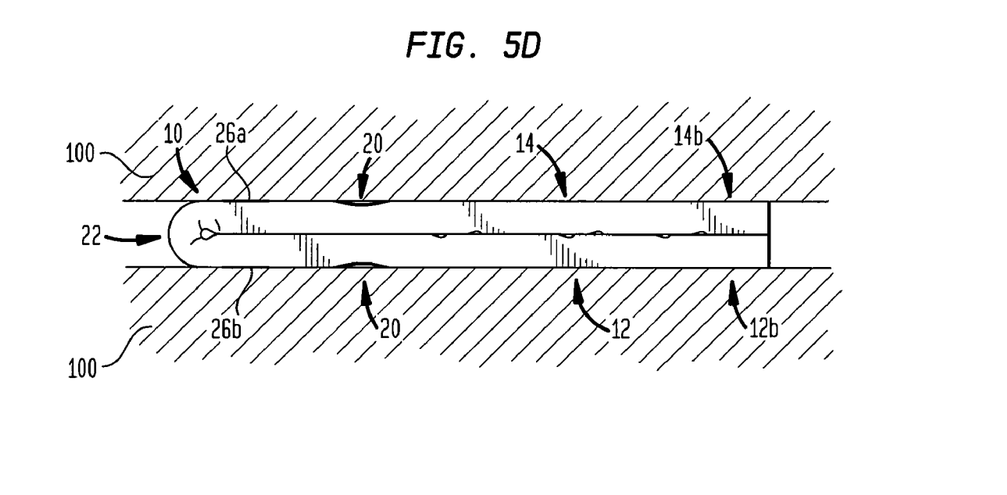
FIG. 5D is a side perspective view of the clip of FIG. 5A fully closed.
Figure 5E:
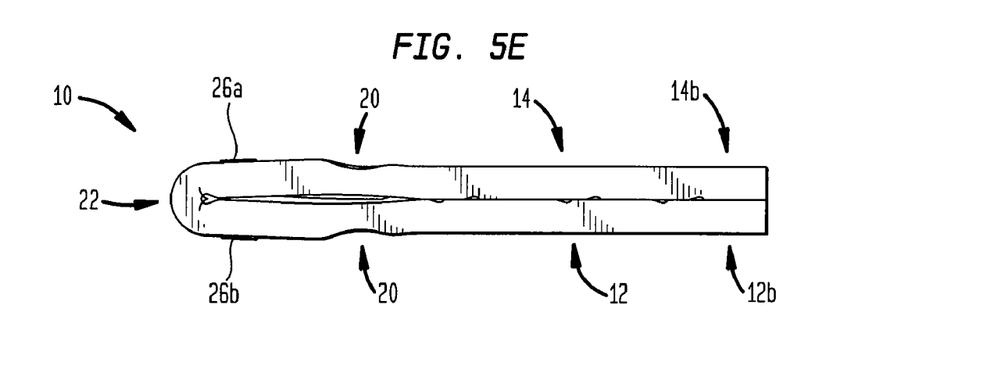
FIG. 5E is a side perspective view of the clip of FIG. 5A following release by a clip applier.

As the application of closing force to the clip 10 continues and the distal ends 12b, 14b of the leg members 12, 14 move closer to one another, the raised area 26 begins to share the clip radial closure forces with the knee portion 20. As a result of this reduction in pressure, the knee 20 is deformed to a lesser extent, as shown in FIG. 5C. FIG. 5D illustrates a condition of full clip closure, with the closing force still applied to the clip 10 by the closing jaws 100. At the final stages of crimping, the raised area 26a, 26b takes some load off of the knee portion 20, thereby reducing the amount of plastic deformation of the knee portion 20. The raised area 26 thus allows the knee portion 20 to have increased elasticity, such that, for example, the knee portion 20 can bend inward slightly when forming loads are released, preloading the tips of the clip 10. This is particularly advantageous in that when the applier is removed from the clip 10 as shown in FIG. 5E, the raised area 26 allows the leg members 12, 14 to remain together from the knee portion 20 to the distal ends 12b, 14b thereof, thereby lessening the duck-billing of the clip 10.

One advantage provided by the clip 10 of the present invention is that it tends to be more resistant to "duck-billing," a condition in which the distal tips of the leg members 12, 14 of the clip 10 tend to separate after the closing force is removed. Some previously known clips tend to duckbill as a result of residual elasticity within the apex. The clip 10 of the present invention is believed to overcome the tendency to duckbill because the apex 22 is able to crimp to a greater extent and thus minimize the effect of any springback. At the same time, increased elasticity between the apex 22 and the knee portion 20 enables any springback at the knee portion 20 to direct the distal ends 12b, 14b of the leg members 12, 14 toward each other. An additional advantage of the above-mentioned characteristics of the clip 10, is that tissue is able to be captured at any location within the clip 10, including near the apex 22 or near the distal ends 12b, 14b of the leg members 12, 14, and still be effectively ligated. As a result, a surgeon can securely ligate vessels having a variety of sizes.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical clip, comprising:
    a pair of opposed first and second leg members having proximal and distal ends with a knee portion formed therebetween, the first and second leg members further including an inner surface having at least one tissue-grasping element formed thereon and a generally planar outer surface having at least one raised area on a portion thereof, wherein the raised area is raised with respect to the outer surface and has a top surface having a width that is less than a width of the outer surface; and
    an apex having opposed ends joining the proximal ends of said first and second leg members, the apex further including at least one notch formed on an inner surface thereof, such that the notch has a width that is less than a width of the inner surface of the apex;
    wherein the raised area is disposed distal to the apex and proximal to the knee portion and the top surface of the raised area is disassociated from the apex.

2. The clip of claim 1, wherein the tissue-grasping element of the first leg member is a longitudinal tongue and the tissue-grasping element of the second leg member is a longitudinal groove.

3. The clip of claim 2, wherein the tongue and the groove are complementary and are disposed opposite to each other.

4. The clip of claim 2, wherein the tongue and groove extend along the entire length of the inner surface of each leg member.

5. The clip of claim 2, wherein the tongue has a height in the range of about 0.0015 inch to about 0.007 inch.

6. The clip of claim 2, wherein the tissue-grasping element of the first and second leg members further includes at least one channel oriented at an angle with respect to the inner surfaces of the first and second leg members.

7. The clip of claim 6, wherein the channel is oriented at an angle of about 45 degrees with respect to a longitudinal axis of the first and second leg members.

8. The clip of claim 1, wherein the notch of the apex is substantially trapezoidal.

9. The clip of claim 1, wherein each leg member has a width less than about 0.05 inch.

10. The clip of claim 9, wherein the clip has a yield strength greater than about 28 ksi.

11. The clip of claim 1, wherein the raised area is a pad disposed proximal to a point approximately midway between the apex and the knee portion of each leg member.

12. The clip of claim 1, wherein the raised area has a height in the range of about 0.0005 inch to about 0.0025 inch.

13. The clip of claim 1, wherein the raised area is a pad.

14. A device for ligating tissue, comprising:
    first and second opposed metallic leg members having proximal and distal ends, and further including inner and outer surfaces, the outer surfaces being generally planar and having one or more raised areas on a portion thereof, wherein the raised areas are raised with respect to the outer surface and each raised area has a top surface having a width that is less than a width of the outer surface;
    a knee portion formed between the proximal and distal ends of each of the leg members; and
    an apex having opposed ends that join the proximal ends of the opposed leg members;
    wherein each of the raised areas is disposed distal to the apex and proximal to the knee portion and the top surface of the raised area is disassociated from the apex.

15. The device of claim 14, wherein the raised area is located approximately one-third of the way between the apex and the knee portion, closer to the apex.

16. The device of claim 14, wherein the raised area has a height in the range of about 0.0005 inch to 0.0025 inch.

17. The device of claim 14, further comprising at least one tissue grasping feature formed on the inner surface of the opposed leg members.

18. The device of claim 17, wherein the tissue-grasping elements include a longitudinal tongue formed on the first leg member and a longitudinal groove formed on the second leg member, the tongue and groove adapted to be complementary to one another.

19. The device of claim 14, wherein the apex includes at least one notch formed on an inner surface thereof.

20. A ligation clip, comprising:
    a pair of opposed metallic legs joined together at a proximal end by an apex, the opposed legs each having a distal end and a knee portion disposed distal of the apex and a raised area formed on a generally planar outer surface of each leg between the apex and the knee portions, wherein the raised area is present on an outer surface of the clip and is raised with respect to the outer surface of each leg;
    the raised area having a top surface that is disassociated from the apex and a width that is less than a width of the outer surface, the raised area being effective to share with the knee portions a load applied by a closing force such that the knee portions are subjected to less plastic deformation and retain some elasticity, wherein upon release of the closing force the distal ends of the clip remain in contact with one another.

21. The device of claim 14, wherein the raised area is a pad.

22. The clip of claim 20, wherein the raised area is a pad.

* * * * *